US 7,925,508 B1

(12) United States Patent
Michaelis (10) Patent No.: US 7,925,508 B1
(45) Date of Patent: Apr. 12, 2011

(54) DETECTION OF EXTREME HYPOGLYCEMIA OR HYPERGLYCEMIA BASED ON AUTOMATIC ANALYSIS OF SPEECH PATTERNS (75) Inventor: Paul Roller Michaelis, Louisville, CO (US)

(73) Assignee: Avaya Inc., Basking Ridge, NJ (US)

( * ) Notice: Subject to any disclaimer, the term of this patent is extended or adjusted under 35 U.S.C. 154(b) by 1161 days.

(21) Appl. No.: 11/508,477

(22) Filed: Aug. 22, 2006

(51) Int. Cl.
*G10L 15/00* (2006.01)
*G10L 15/06* (2006.01)
*A61B 5/00* (2006.01)
*A61B 5/0432* (2006.01)
*G10L 21/00* (2006.01)
*G10L 11/00* (2006.01)

(52) U.S. Cl. ........ 704/270; 704/231; 704/272; 600/300; 600/529; 600/532

(58) Field of Classification Search .................. 704/231, 704/234–240, 243–255, 268, 270, 272, 274, 704/E51.001–E51.05, E11.001–E11.007; 379/52, 201.01–201.1, 265.01–266.1; 381/54; 600/300, 481, 529, 531–543
See application file for complete search history.

(56) References Cited

U.S. PATENT DOCUMENTS

| | | | |
|---|---|---|---|
| 4,156,423 A * | 5/1979 | Friedman et al. | 600/508 |
| 4,468,804 A | 8/1984 | Kates et al. | |
| 4,696,039 A | 9/1987 | Doddington | |
| 4,838,275 A * | 6/1989 | Lee | 600/483 |
| 4,852,170 A | 7/1989 | Bordeaux | |
| 5,018,200 A | 5/1991 | Ozawa | |
| 5,206,903 A | 4/1993 | Kohler et al. | |
| 5,583,969 A | 12/1996 | Yoshizumi et al. | |
| 5,634,086 A | 5/1997 | Rtischev et al. | |
| 5,644,680 A | 7/1997 | Bielby et al. | |
| 5,684,872 A | 11/1997 | Flockhart et al. | |
| 5,722,418 A * | 3/1998 | Bro | 600/545 |
| 5,796,948 A | 8/1998 | Cohen | |
| 5,802,149 A | 9/1998 | Hanson | |
| 5,828,747 A | 10/1998 | Fisher et al. | |
| 5,868,135 A * | 2/1999 | Kaufman et al. | 600/300 |
| 5,905,793 A | 5/1999 | Flockhart et al. | |
| 5,982,873 A | 11/1999 | Flockhart et al. | |
| 6,064,731 A | 5/2000 | Flockhart et al. | |
| 6,084,954 A | 7/2000 | Harless et al. | |
| 6,088,441 A | 7/2000 | Flockhart et al. | |
| 6,122,614 A | 9/2000 | Kahn et al. | |
| 6,151,571 A | 11/2000 | Pertrushin | |

(Continued)

FOREIGN PATENT DOCUMENTS

CA  1333425  12/1994

(Continued)

OTHER PUBLICATIONS

"What are symptoms of hypoglycemia?" Essortment.com. Posted Nov. 27, 2005. Accessed via Internet archive Aug. 23, 2010. <http://web.archive.org/web/20051127014722/va.essortment.com/hypoglycemiasym_rjfc.htm>.*

(Continued)

*Primary Examiner* — James S Wozniak
*Assistant Examiner* — David Kovacek
(74) *Attorney, Agent, or Firm* — Sheridan Ross P.C.

(57) ABSTRACT

In one embodiment, the present invention is directed to a communication device that analyzes received utterances and detects when the speaker has a target physical condition.

18 Claims, 3 Drawing Sheets

U.S. PATENT DOCUMENTS

| | | | |
|---|---|---|---|
| 6,163,607 | A | 12/2000 | Bogart et al. |
| 6,173,053 | B1 | 1/2001 | Bogart et al. |
| 6,178,400 | B1 | 1/2001 | Eslambolchi |
| 6,192,122 | B1 | 2/2001 | Flockhart et al. |
| 6,243,680 | B1 | 6/2001 | Gupta et al. |
| 6,259,969 | B1 | 7/2001 | Tackett et al. |
| 6,275,806 | B1 | 8/2001 | Pertrushin |
| 6,275,991 | B1 | 8/2001 | Erlin |
| 6,278,777 | B1 | 8/2001 | Morley et al. |
| 6,292,550 | B1 | 9/2001 | Burritt |
| 6,314,165 | B1 | 11/2001 | Junqua et al. |
| 6,353,810 | B1 | 3/2002 | Petrushin |
| 6,363,346 | B1 | 3/2002 | Walters |
| 6,374,221 | B1 | 4/2002 | Haimi-Cohen |
| 6,389,132 | B1 | 5/2002 | Price |
| 6,408,273 | B1 | 6/2002 | Quagliaro et al. |
| 6,427,137 | B2 | 7/2002 | Petrushin |
| 6,463,415 | B2 | 10/2002 | St. John |
| 6,480,826 | B2 | 11/2002 | Pertrushin |
| 6,643,622 | B2 | 11/2003 | Stuart et al. |
| 6,690,940 | B1* | 2/2004 | Brown et al. ............... 455/456.4 |
| 6,697,457 | B2 | 2/2004 | Petrushin |
| 6,766,014 | B2 | 7/2004 | Flockhart et al. |
| 6,801,888 | B2 | 10/2004 | Hejna, Jr. |
| 6,823,312 | B2 | 11/2004 | Mittal et al. |
| 6,839,669 | B1 | 1/2005 | Gould et al. |
| 6,847,714 | B2 | 1/2005 | Das et al. |
| 6,889,186 | B1 | 5/2005 | Michaelis |
| 6,940,951 | B2 | 9/2005 | Mahoney |
| 6,979,298 | B2* | 12/2005 | Vodyanoy et al. ............ 600/529 |
| 6,999,563 | B1 | 2/2006 | Thorpe et al. |
| 7,065,485 | B1 | 6/2006 | Chong-White et al. |
| 7,180,997 | B2 | 2/2007 | Knappe |
| 7,222,074 | B2 | 5/2007 | Zhou |
| 7,222,075 | B2 | 5/2007 | Petrushin |
| 7,261,691 | B1* | 8/2007 | Asomani ....................... 600/300 |
| 7,267,652 | B2 | 9/2007 | Coyle et al. |
| 7,398,213 | B1* | 7/2008 | Levanon et al. ............... 704/271 |
| 7,490,085 | B2* | 2/2009 | Walker et al. ........................ 1/1 |
| 2002/0084130 | A1 | 7/2002 | Der Ghazarian et al. |
| 2003/0009341 | A1* | 1/2003 | Cheng et al. .................. 704/275 |
| 2003/0096594 | A1* | 5/2003 | Naboulsi ....................... 455/411 |
| 2003/0191639 | A1 | 10/2003 | Mazza |
| 2004/0039261 | A1* | 2/2004 | Bardy .......................... 600/300 |
| 2004/0054263 | A1* | 3/2004 | Moerman et al. ............. 600/300 |
| 2004/0148161 | A1 | 7/2004 | Das et al. |
| 2004/0148356 | A1 | 7/2004 | Bishop et al. |
| 2004/0215453 | A1 | 10/2004 | Orbach |
| 2005/0010416 | A1* | 1/2005 | Anderson et al. ............. 704/271 |
| 2005/0065789 | A1 | 3/2005 | Yacoub et al. |
| 2005/0094822 | A1 | 5/2005 | Swartz |
| 2005/0163302 | A1 | 7/2005 | Mock et al. |
| 2005/0228234 | A1* | 10/2005 | Yang ............................ 600/300 |
| 2005/0241871 | A1 | 11/2005 | Stewart et al. |
| 2006/0009257 | A1 | 1/2006 | Ku |
| 2006/0020466 | A1* | 1/2006 | Cousineau et al. ........... 704/257 |
| 2006/0028556 | A1* | 2/2006 | Bunn et al. ................ 348/211.99 |
| 2006/0036437 | A1 | 2/2006 | Bushey et al. |
| 2006/0058697 | A1* | 3/2006 | Mochizuki et al. ........... 600/532 |
| 2006/0148490 | A1 | 7/2006 | Bates et al. |
| 2006/0167595 | A1 | 7/2006 | Breed et al. |
| 2006/0183980 | A1* | 8/2006 | Yang ............................ 600/301 |
| 2006/0203992 | A1 | 9/2006 | Kim |
| 2006/0212195 | A1 | 9/2006 | Veith et al. |
| 2006/0229505 | A1* | 10/2006 | Mundt et al. .................. 600/300 |
| 2006/0252376 | A1 | 11/2006 | Fok |
| 2006/0271404 | A1 | 11/2006 | Brown |
| 2007/0038455 | A1 | 2/2007 | Murzina |
| 2007/0106127 | A1* | 5/2007 | Alman .......................... 600/300 |
| 2007/0124135 | A1 | 5/2007 | Schultz ........................ 704/201 |
| 2007/0173726 | A1* | 7/2007 | Kim et al. ..................... 600/483 |

FOREIGN PATENT DOCUMENTS

| | | |
|---|---|---|
| EP | 0076687 | 4/1983 |
| EP | 0140249 | 5/1985 |
| EP | 0360265 | 3/1990 |
| JP | 10-124089 | 5/1998 |
| WO | WO 00/22611 | 4/2000 |
| WO | WO 2004/056086 | 7/2004 |

OTHER PUBLICATIONS

Kawaguchi et al. "Development of a telenursing system for patients with chronic conditions." Journal of Telemedicine and Telecare; 2004; 10, 4; ProQuest Health and Medial Complet. p. 239.*

Black, et al. "Implementing autonomy in a diabetes management system." Journal of Telemedicein and Telecare; 2005; 11 Suppl 1. p. 6-8.*

"Voice-dialgoue system eases diabetes monitoring." The British Journal of Healthcare Computing & Information Management; Oct. 2005; 22, 8; ProQuest Health and Medical Complete. p. 25.*

"Symptoms of Diabetes." WrongDiagnosis.com. Published Jun. 27, 2003. Accessed Aug. 23, 2010 via Internet Archive. <http://web.archive.org/web/20030627021518/http:/www.wrongdiagnosis.com/d/diabetes/symptoms.htm>.*

"Hypoglycemia." MedicineNet.com. Published Jan. 19, 2006. Accessed Aug. 23, 2010 via Internet Archive. p. 2 of 4. <http://web.archive.org/web/20060119000857/http:/www.medicinenet.com/hypoglycemia/page2.htm>.*

"Hyperglycemia (High Blood Sugar)." University of Iowa Hopstials & Clinics. Published Mar. 23, 2006. Accessed Sep. 9, 2010 via Internet Archive. <http://web.archive.org/web/20060323081940/http://www.uihealthcare.com/topics/diabetes/hyperglycemia.html>.*

U.S. Appl. No. 11/388,694, filed Mar. 24, 2006, Blair et al.

U.S. Appl. No. 10/882,975, filed Jun. 30, 2004, Becker et al.

Landauer et al., "An Introduction to Latent Semantic Analysis", Discourse Processes, 1998, 41 pages.

Lin et al., "Phoneme-less Hierarchical Accent Classification", HP Laboratories Palo Alto, Oct. 4, 2004, 5 pages.

Michaelis, "Speech Digitization and Compression", In W. Warkowski (Ed.), International Encyclopedia of Ergonomics and Human Factors. London: Taylor Francis, 2001, 683-686.

U.S. Appl. 10/756,669, filed Jan. 12, 2004, Thambiratnam

U.S. Appl. No. 11/131,108, filed May 16, 2005, Michaelis.

"Assistive Writing," AbilityHub.com (printed Apr. 11, 2005), available at http://www.abilityhub.com/speech/speech-Id.htm, 2 pages.

"Automatic Speech Recognition," Technology Access Program, AbilityHub.com (Fall 2002), available at http://tap.gallaudet.edu/SpeechRecog.htm, 2 pages.

"Contrasts in Pronunciation," (undated), available at http://www.bohemica.com/czechonline/reference/pronunciation/contrasts.htm, 2 pages.

"Inside Speech Recognition," (printed Apr. 11, 2005), available at http://fsug.org/usyd.edu.au/documentation/HOWTO/Speech-Recognition-HOWTO/inside...., 2 pages.

"Speech Recognition," (printed Apr. 11, 2005) available at http://murray.newcastle.edu.au/user/staff/speech/home_pages/tutorial_sr.html, 5 pages.

Arslan, Levent M., "Foreign Accent Classification in American English," thesis, pp. 1-200, Department of Electrical Computer Engineering, Duke University, 1996.

Arslan, Levent M., et al., "Language Accent Classification in American English," Robust Speech Processing Laboratory Department of Electrical Engineering, Durham, North Carolina, Technical Report RSPL-96-7(1996).

Hansen, John H.L., et al., "Foreign Accent Classification Using Source Generator Based Prosodic Features," IEEE Proc. ICASSP, vol. 1, Detroit U.S.A., (1995), pp. 836-839.

Hosom, John-Paul, et al., "Training Neural Networks for Speech Recognition," Center for Spoken Language Understanding, Oregon Graduate Institute of Science and Technology (Feb. 2, 1999), 51 pages.

Jackson, Philip J.B., et al., "Aero-Acoustic Modeling of Voiced and Unvoiced Fricatives Based on MRI Data," University of Birmingham and University of Southampton, (undated), 4 pages.

Kirriemuri, John, "Speech Recognition Technologies," TSW 03-03 (Mar. 2003), 13 pages.

Lamel, L.F., et al., "Language Identification Using Phone-based Acoustic Likelihoods," ICASSP-94.

Laramee, François Dominic, "Speech Interfaces for Games—Part 1: How Speech Recognition Words," GIGnews.com (2000), available at http://www.gignews.com/fdlspeech2.htm, 5 pages.

Loizou, Philip, "Speech Production and Perception," EE 6362 Lecture Notes (Fall 2000), pp. 1-30.

Markowitz, J., "Glossaries," available at http://www.jmarkowitz.com/glossary.html, 4 pages.

Michaelis, Paul Roller, "Speech Digitization and Compression," Avaya Laboratories (undated), pp. 1-5.

Noth, E., et al., "Research Issues for the Next Generation Spoken"; University of Erlangen-Nuremberg, Bavarian Research Centre for Knowledge-Based Systems, at http://www5.informatik.uni-erlangen.de/literature/psdir/1999/Noeth99:RIF.ps.gz, downloaded Feb. 10, 2003.

Pervasive, Human-Centered Computing, MIT Project Oxygen, MIT Laboratory for Computer Science, Jun. 2000.

Zue, Victor, "The MIT Oxygen Project," MIT Laboratory for Computer Science, Apr. 25-26, 2000.

Background of the Invention for the above-captioned application (previously provided).

"Module 3"; Available at: http://www.dendrites.com/mod3r.html; Undated; 244 pages.

Aviation Safety Investigation Report; Available at: http://64.233.167.104/search?q=cache:xL7YYq5EvwsJ:www.atsb. gov.au/aviation/pdf/200204328.pdf+%22speech+analysis%22+%22detect%22+and+%22state+of+intoxication% 22&hl=en&gl=us&ct=clnk&cd=1; Undated; 151 pages; Australian Transport Safety Bureau.

"Dialing Under the Influence" Available at: http://www.virginmobile.com.au/services/duti.html; 2006; 2 pages; Virgin Mobile.

"Module 4, Autonomic Nervous System: Clinical Implications and Non Pharmaceutical Applications."; Available at: http://www.dendrites.com/module4.htm; Undated; 39 pages.

"Agile Lie Detector"; Available at: http://www.agilemobile.com/agile_liedetector.html; 2004; 1 page; Agilemobile.com.

De-FIB-ulator Portable "Lie Detector"; Available at: http://www.sharperimage.com/us/en/catalog/product/sku_AR002; 2006; 2 pages; The Sharper Image.

"Lie Detection and A Major Breakthrough in Price and Portability!"; Available at: http://www.pimall.com/nais/e.pse.html; 2006; Thomas Investigative Publications, Inc.; Austin, Tx.

Hollien H.; "Production of intoxication states by actors—acoustic and temporal characteristics."; J. Forensic Sci.; Jan. 2001; 46(1); pp. 68-73; Two-page internet summary available at http://www.ncbi.nlm.nih.gov/entrez/query.fcgi?db=pubmed&cmd=Retrieve&dopt=Abstract&list_uids=11210927&query_hl=3&itool=pubmed_ExternalLink.

Johnson K.; "Do voice recordings reveal whether a person is intoxicated? A case study."; Phonetica; 1990; 47(3-4); pp. 215-237; One-page internet summary available at http://www.ncbi.nlm.nih.gov/entrez/query.fcgi?db=pubmed&cmd=Retrieve&dopt=Abstract&list_uids=2130381&query_hl=5&itool=pubmed_ExternalLink.

Pisoni DB.; "Effects of alcohol on the acoustic-phonetic properties of speech: perceptual and acoustic analyses."; Alcohol Clin Exp Res.; Aug. 1989; 13(4); pp. 577-587; One-page internet summary available at http://www.ncbi.nlm.nih.gov/entrez/query.fcgi?db=pubmed&cmd=Retrieve&dopt=Abstract&list_uids=2679214&query_hl=7&itool=pubmed_ExternalLink.

U.S. Appl. No. 11/508,442, filed Aug. 22, 2006, Coughlan.

U.S. Appl. No. 11/768,567, filed Jun. 26, 2007, Coughlan.

Watson PI, Ciccia AH, Weismer G (2003), The relation of lung volume initiation to selected acoustic properties of speech. J Acoust Soc Am 113 :2812-2819.

Novak, D Cuesta-Frau, and L. Lhotska: Speech recognition methods applied to biomedical signals processing. Engineering in Medicine and Biology Society. 2004; 1: 118-121.

Entwistle, The performance of automated speech recognition systems under adverse conditions of human exertion. Int. J. Hum.-Comput. Interact. 16 (2003) (2), pp. 127-140.

Entwistle, "Training Methods and Enrollment Techniques to Improve the Performance of Automated Speech Recognition Systems Under Conditions of Human Exertion", A Dissertation Submitted in Partial Fulfillment of The Requirements for the Degree of Doctor of Philosophy, University of South Dakota, Jul. 2005.

McCarthy, Caroline. "New cell phone to prevent drunk dialing." CNET News. Jun. 28, 2006 Accessed online Mar. 19, 2010. <http://news.cnet.com/8301-1 0784_3-6088879-7. html>.

Official Action for U.S. Appl. No. 11/508,442, mailed Mar. 26, 2010.

* cited by examiner

DETECTION OF EXTREME HYPOGLYCEMIA OR HYPERGLYCEMIA BASED ON AUTOMATIC ANALYSIS OF SPEECH PATTERNS

CROSS REFERENCE TO RELATED APPLICATION

Cross reference is made to U.S. patent application Ser. No. 11/508,442 filed concurrently herewith, entitled "DYNAMIC USER INTERFACE FOR THE TEMPORARILY IMPAIRED BASED ON AUTOMATIC ANALYSIS FOR SPEECH PATTERNS", to Coughlan, et al., which is incorporated herein by this reference.

FIELD OF THE INVENTION

The invention relates generally to speech analysis and particularly to analysis of speech to identify a selected physical condition or state of a user.

BACKGROUND OF THE INVENTION

Diabetics must monitor their blood sugar levels directly to ensure that these levels remain within an acceptable range. When blood sugar levels drop below a first threshold, the diabetic suffers from a physical condition known as hypoglycemia and, when blood sugar levels rise above a second threshold, the diabetic suffers from a physical condition known as hyperglycemia.

Although mild hypoglycemia and hyperglycemia are common among diabetics, and generally regarded as manageable, moderate or extreme hypoglycemia and hyperglycemia can be life-threatening. When in either condition, the diabetic is often unable to think clearly, and may therefore be unaware that a dangerous condition exists. Failure to take prompt corrective action, such as consuming sugar when the diabetic is hypoglycemic or receiving an insulin injection when the diabetic is hyperglycemic, can result in serious medical complications. As either condition worsens, the diabetic can enter into a diabetic coma, which may result in death.

To avoid either condition, the diabetic must maintain his or her blood sugar level within an acceptable range. This is preferentially done by frequent, regular monitoring of his or her blood sugar level. This is typically done by pricking the finger in order to obtain a sample of blood, placing the blood on a disposable test strip, and then relying on a machine to perform chemical or optical analyses of the blood to determine the sugar level. Many diabetics find this procedure to be bothersome, if not painful, and are not diligent about checking blood sugar levels. Even more problematical, the test strips, which are typically not reusable, are commonly quite expensive. Because of the inconvenience, discomfort and cost, many diabetics do not test their blood appropriately, and therefore fail to discover the presence of hypoglycemia or hyperglycemia. Among diabetics who do not monitor their blood sugar levels diligently, the progression of mild conditions to conditions requiring medical attention is an all-too-frequent occurrence.

There is a need for a noninvasive, unobtrusive technique to detect the possible onset of hypo- or hyperglycemia.

SUMMARY OF THE INVENTION

These and other needs are addressed by the various embodiments and configurations of the present invention. The present invention is generally directed to the use of speech uttered in the course of a multi-person communication, such as a telephone call, to evaluate the physical state of the speaker.

In a first embodiment, a method for determining a physical state of a user includes the steps of:

(a) a communication device receiving a voice utterance from a speaker;

(b) analyzing the voice utterance to determine whether the speaker likely has an involuntary target physical condition (e.g., hypoglycemia, hyperglycemia, and/or seizure); and (c) when the speaker likely has the target physical condition, sending to the user a notification associated with the target physical condition and/or to a third party a notification associated with the target physical condition.

The analysis can be acoustic-phonetic analysis of the voice utterance to determine the likelihood that the speaker has the target physical condition and/or a likely severity of the target physical condition. The acoustic-phonetic analysis analyzes, with reference to a baseline utterance of the speaker, one or more of a formant of the utterance, a pitch of the utterance, a speech and/or articulation rate of the utterance, a vocal intensity of the utterance, a number of speech errors in the utterance, a response time, a nonfluency level associated with the utterance, and a speech quality of the utterance.

In one configuration, the analysis is performed by comparing speech units in the utterance with corresponding baseline speech units obtained from the same speaker when that speaker did not have the target physical condition, and, based on the comparative results of the prior steps, determining a level of confidence that the speaker has and/or does not have the target physical condition.

In one configuration, the method determines both the likelihood that the speaker has the target physical condition and likely severity of the target physical condition. When the likelihood and likely severity are at least a first set of thresholds, a third party (e.g., primary caregiver, emergency personnel, etc.) (in addition to the speaker) is notified of the potential physical condition of the user, and, when the likelihood and likely severity is less than the first set of thresholds but more than a second set of thresholds, the speaker only is notified of his or her potential physical condition.

The present invention can provide a number of advantages depending on the particular configuration. For example, it can provide a noninvasive way of detecting potentially serious medical conditions of a speaker. The analysis is performed whenever the speaker contacts a telecommunication device of another party, whether the speaker engages in a conversation with the other party or simply leaves a voice message on the other party's voice messaging system. The utterances are compared to baseline utterances that were recorded when the speaker was known to have a normal physical condition (e.g., a normal blood sugar level).

These and other advantages will be apparent from the disclosure of the invention(s) contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The above-described embodiments and configurations are neither complete nor exhaustive. As will be appreciated, other embodiments of the invention are possible utilizing, alone or in combination, one or more of the features set forth above or described in detail below.

DETAILED DESCRIPTION

Overview of the Network Architecture

Figure 1:
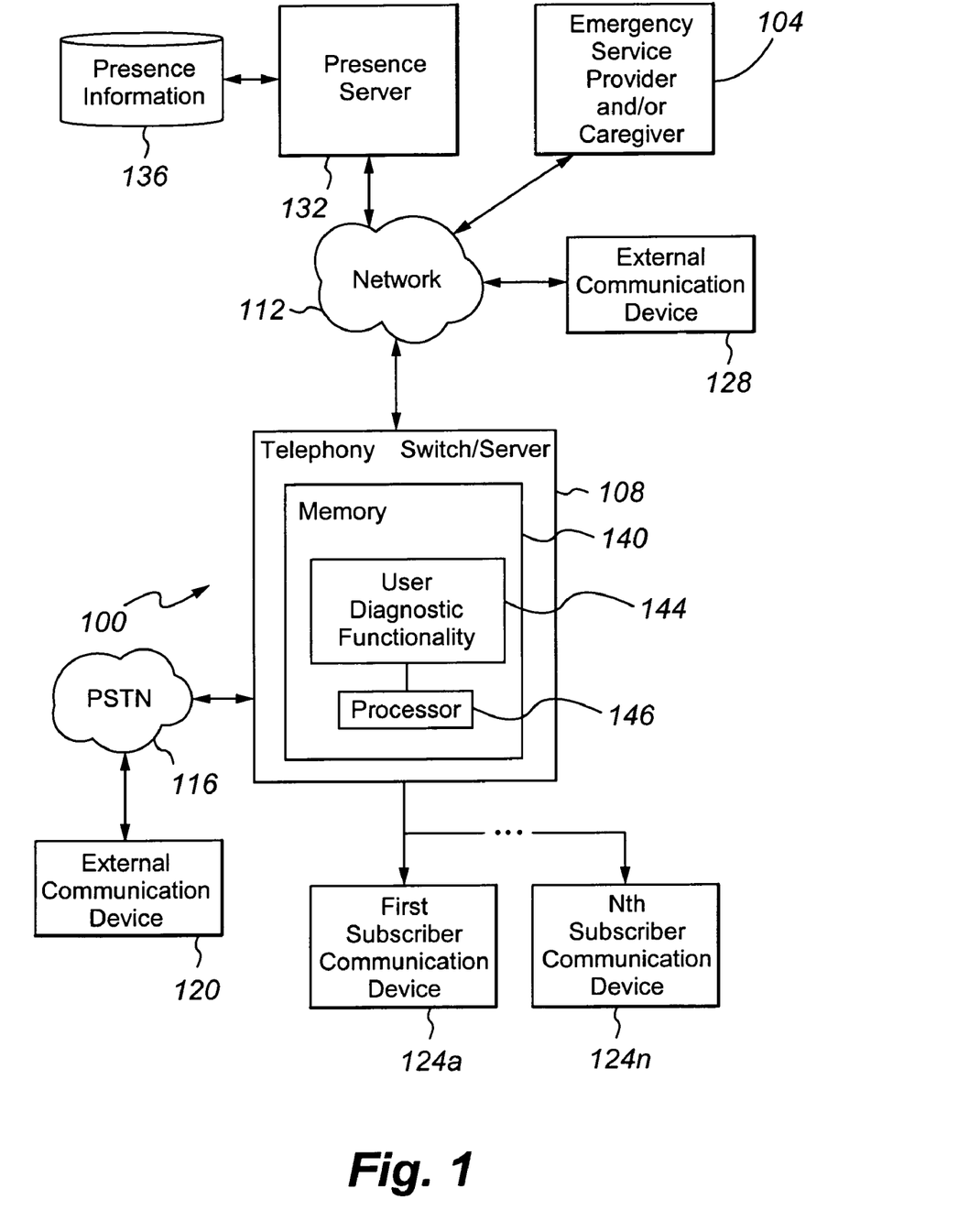
FIG. 1 is a block diagram of an enterprise architecture according to an embodiment of the present invention.

FIG. 1 depicts a presence aware communications network according to a first architecture of the present invention. The presence aware communications network 100 comprises an emergency service provider and/or primary caregiver 104 that is notified in the event of an alarm condition, a telephony switch/server 108 for directing contacts, a packet-switched network 112, a circuit-switched Public Switched Telephone Network or PSTN 116, a first set of internal subscriber communication devices 124a-n controlled by the telephony switch/server 108, a second external communication device 120 in communication with PSTN 116, a third external communication device 128 in communication with the network 112, and a presence server 132 and associated presence information database 136 for providing presence information about one or more users of the various communication devices. As will be appreciated, presence aware network components can be implemented in software and/or hardware, depending on the application.

The internal communication devices 124a-n have extensions within the premises that are directly serviced by the switch. More particularly, these extensions correspond to conventional terminal endpoints serviced by the switch/server 108, and the switch/server 108 can direct incoming calls to and receive outgoing calls from these extensions in a conventional manner. The second and third communication devices 120 and 128 are referred to as "external" in that they are not directly supported as terminal endpoints by the switch/server 108.

The emergency service provider and/or primary caregiver 104 is associated with one or more packet-switched and/or circuit switched wireless or wired communication devices and is notified when the user diagnostic functionality 144 in the switch/server 108 detects an alarm condition. The alarm condition is typically indicative of the physical state or condition of a subscriber.

The telephony switch/media server 108 can be any architecture for directing contacts to one or more communication devices. Illustratively, the switch/server 108 of FIG. 1 can be a modified form of the subscriber-premises equipment disclosed in U.S. Pat. Nos. 6,192,122; 6,173,053; 6,163,607; 5,982,873; 5,905,793; 5,828,747; and 5,206,903, all of which are incorporated herein by this reference; Avaya Inc.'s Definity™, Multi-Vantage™, or Communication Manager™ private-branch exchange (PBX)-based ACD system; or Avaya Inc.'s IP Office™. The switch or media server 108 typically is a stored-program-controlled system that conventionally includes interfaces to external communication links, a communications switching fabric, service circuits (e.g., tone generators, announcement circuits, etc.), memory 140 for storing control programs and data, and a processor 146 (i.e., a computer) for executing the stored control programs to control the interfaces and the fabric and to provide automatic contact-distribution functionality. The switch/server 108 comprises a network interface card to provide services to the subscriber communication devices 124a-n. Included in the memory 140 is the user diagnostic functionality 144 that monitors the voice streams of selected subscribers to detect a physical state or condition of the subscriber, such as a hypoglycemia, hyperglycemia, and epileptic seizure (e.g., a grand mal or petit mal seizure). Switch-server 108 can include a gateway (not shown) to provide signal control and conversion capabilities between the circuit-switched PSTN 116 or some other type of circuit-switched network and the packet-switched network 112.

The packet-switched network 112 can be any data and/or distributed processing network, such as the Internet. The network 112 typically includes proxies, registrars, and routers for managing packet flows.

The set of first subscriber communication devices 124a-n and second and third communication devices 120 and 128, respectively, can be any communication device suitable for the network to which they are connected. The first set of communication devices 124a-n are packet-switched and/or circuit-switched and can include, for example, IP hardphones, IP softphones, Personal Digital Assistants or PDAs, Personal Computers or PCs, and laptops. The second and third communication devices 120 and 128 are commonly circuit-switched and can include, for example, wired and wireless telephones, PDAs, pagers, facsimile machines, and modems.

The presence server 132 collects published presence information about a communication device and/or user thereof and stores the collected information in the presence information database 136. The database 136 further includes permissible personal information about the subscriber, such as name, home and business addresses, and medical information. The presence server typically retrieves presence information by querying against the user's identity as opposed to the device address. In the presence information database all presence information is indexed by a user's identity rather than device address. The presence server 132 provides the collected information to other network entities in response to queries. The presence server 132 can collect only information respecting the user's interaction with the various entities of FIG. 1 and/or other information provided directly or indirectly by the user when those entities publish their presence information to the presence server. The presence server 132 can interact with additional presence services (now shown) that continually collect and redistribute availability data from publishing sources authorized by the user.

The User Diagnostic Functionality

It is well known that changes in speech patterns are common among people who are suffering from hypoglycemia or hyperglycemia. For example, hypoglycemia—which is often accompanied by feelings of anxiety—commonly causes people to speak more rapidly and with greater urgency. By contrast, hyperglycemia is often accompanied by feelings of lethargy, thereby causing speech patterns that may be slow or slurred. Although these effects tend to vary considerably among different individuals, a key point is that the speech patterns of individuals with hypoglycemia or hyperglycemia can be expected to deviate in a measurable way from patterns obtained when that individual's blood chemistry was in a normal range.

Included in the memory 140 is the user diagnostic functionality, which monitors and analyzes selected subscriber's voice streams to detect a corresponding physical state of the subscriber. The voice stream can be received when the subscriber is using any of the internal and external communication devices as part of a contact or call. The term "contact" or "call" as used herein is intended to include not only telephone calls but also non-telephonic communications, such as data transmissions such as electronic mail, voice-over-IP, facsimile, etc., whether circuit switched or packet switched. When a selected (target) physical state is detected, the functionality 144 takes appropriate actions, including, in increasing order of importance, visually and/or auditorally notifying the user of the determination (e.g., "you may be suffering from hypoglycemia", "you may be suffering from hyperglycemia", etc.), suggesting to the user a recommended course of action (e.g., checking blood sugar levels immediately, contacting a primary caregiver, etc.), notifying a nearby employee or primary caregiver to check on the condition of the subscriber, and notifying emergency personnel that the subscriber may be suffering from extreme hypoglycemia or hyperglycemia. As part of the third party notification, the functionality 144 can query the presence server 132 for presence information associated with the user and include the information to the third party notification. The presence information could include, for example, contact information respecting a communication device at which the user is currently available and/or a current physical location of the user. The functionality can determine the degree of severity of the physical condition by analysis of the degree or extent of deviation of the subscriber's speech from a baseline condition.

The analysis is typically performed using selected units of speech. Human speech is affected by the unique interaction of the lungs, trachea (windpipe), larynx, pharyngeal cavity (throat), oral cavity (mouth), and nasal cavity. The pharyngeal and oral cavities are known as the vocal tract. The vocal folds (cords), soft palate or velum, tongue, teeth, and lips move to different positions to produce various speech sounds and are known as articulators. Any part of the original pitch that is near a resonance frequency of the vocal tract are amplified while any part that is not near the resonance frequency is attenuated. As the relative positions of the articulators are altered, the vocal tract resonance frequency is changed. The vocal tract resonances thus become variable points of amplification of the original excitation signal and are referred to as formants.

Depending on the type of excitation by the larynx and lungs, two types of sounds can be produced, namely voiced and unvoiced sounds or utterances. As used herein, an "utterance" refers to any speech component that is uttered or audibly expressed by a person, including sentences, phrases, words, portions of words, and letters. Voiced speech sounds (for example, the "V" sound in "voice") are produced by tensing the vocal cords while exhaling. The tensed vocal cords briefly interrupt the flow of air, releasing it in short periodic bursts. The greater the frequency with which the bursts are released, the higher the fundamental pitch. Unvoiced sounds (for example, the final "S" sound in "voice") are produced when air is forced past relaxed vocal cords. The relaxed cords do not interrupt the air flow; the sound is instead generated by audible turbulence in the vocal tract. A simple demonstration of the role of the vocal cords in producing voice and unvoiced sounds can be had by placing one's fingers lightly on the larynx, or voice box, while slowly saying the word "voice." The vocal cords will be felt to vibrate for the "V" sound and for the double vowel (or diphthong) "oi" but not for the final "S" sound.

Except when whispering, all vowel and nasal sounds in spoken English are voiced. Plosive sounds—also known as stops—may be voiced or unvoiced. Examples of voiced plosives include the sounds associated with "B" and "D". Examples of unvoiced plosives include the sounds associated with "P" and "T." Fricative sounds may also be voiced or unvoiced. Examples of voiced fricatives include the sounds associated with "V" and "Z." Examples of unvoiced fricatives include the sounds associated with "F" and "S."

The movement and location of the tongue, jaw, and lips are identical for the "B" and "P" sounds, the only difference being whether the sounds are voiced. The same is true of the "D" and "T" pair, the "V" and "F" pair, and the "Z" and "S" pair.

When a person suffers from certain physical conditions, the speech units deviate, sometimes substantially, from the baseline speech unit for the same person. For example, when a diabetic is hypoglycemic, he or she can become nervous or agitated. This can cause the person to speak more rapidly. Illustratively, one way that this could be detected automatically with minimal effort is to measure the number of acoustic transitions—e.g., transitions between voiced and unvoiced speech sounds—that occur within a specific unit of time. When the diabetic is hyperglycemic, he or she can have slurred speech and delayed responses, as if intoxicated. Illustratively, one way slurring could be detected automatically is to determine whether the spectral content of what are supposed to be "S" sounds has shifted downward toward what is commonly seen with "SH" sounds; delayed responsiveness could be detected by measuring the duration of silences at points in a conversation where the user would be expected to speak. By comparing a set of characteristics of speech units against a baseline set of characteristics for the same speech units, the functionality 144 can detect not only that the subscriber is likely suffering from a deviant or target physical condition but also the type and severity of the target physical condition.

The set of characteristics can be any measure or set of auditory and/or acoustic-phonetic measures, such as fundamental frequency (pitch or F0), formant or F-pattern, speech or articulation rate, vocal intensity (loudness), speech errors, response time, nonfluency level, and aspects of speech quality. A hypoglycemic speaker may, for example, have (relative to baseline characteristics under normal conditions) a pronounced increase in pitch, vocal intensity, and speech or articulation rate. When the diabetic is suffering from hyperglycemia, there may be (relative to baseline characteristics under normal conditions) a decrease in speech or articulation rate, misarticulation of specific difficult voiced and unvoiced sounds, such as fricatives and plosives (e.g., "r" to "l", "s" to "sh", "ez" to "es"), an increase in the fundamental frequency, and an increase in the number of speech errors or nonfluencies per unit time. Speech and articulation rates are both durational measurements in terms of the number of syllables per second. Speech rate is calculated by dividing the duration of the entire utterance, including any pauses, by the total number of syllables in the'utterance. Articulation rate is calculated in a similar way, except that the silent pauses within the utterance are not included in the calculation.

Different speech sounds are typically articulated with different time frames; that is, some speech sounds take longer to articulate than others. To maintain comparability when calculating articulation rates over relatively small quantities of data, such as short utterances, it is preferable to calculate articulation rate over a linguistically equivalent utterance. For example, a linguistically equivalent utterance would have the same set of words, such as "Hello, this is Mike", "How are you doing today?", "How can I help you?", etc.

Figure 2:
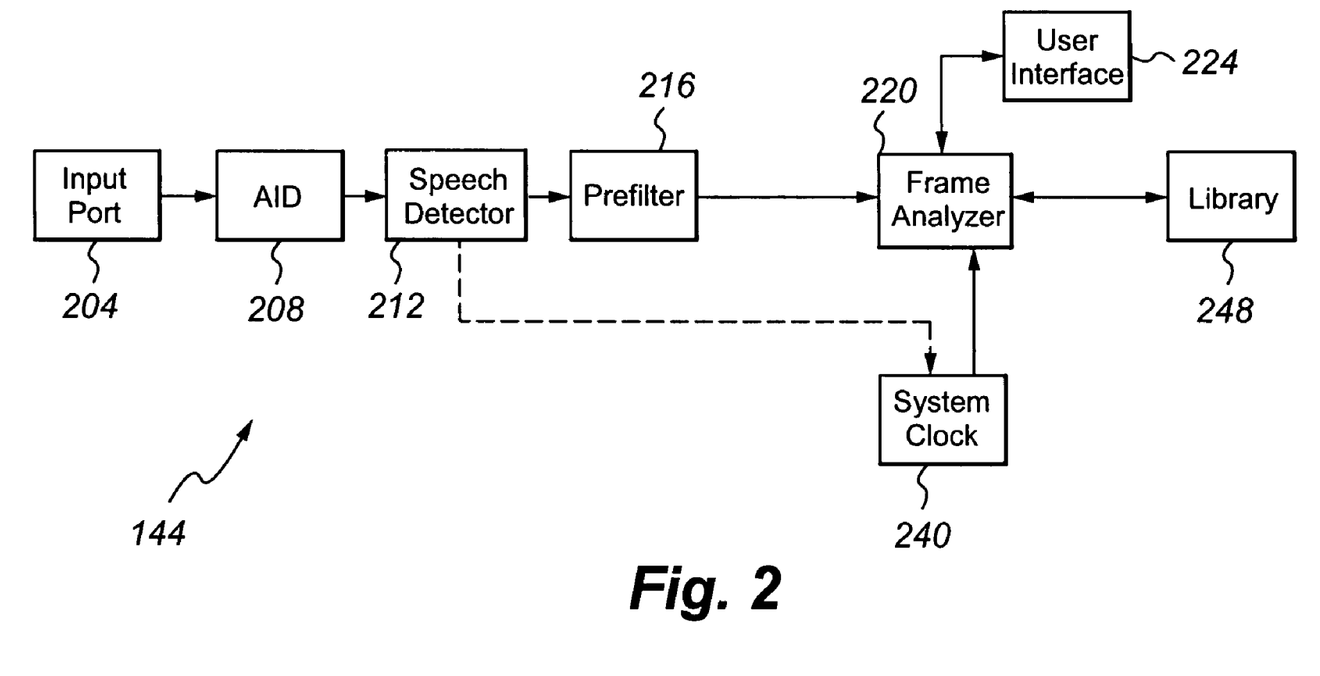
FIG. 2 is a block diagram of the components of the user diagnostic functionality according to an embodiment of the present invention.

FIG. 2 depicts the various computational modules forming the user diagnostic functionality 144. The functionality 144 receives an analog speech signal at an input port 204 (such as a microphone) and converts this signal to a text equivalent of the digital speech signal. In one configuration, the functionality 144 matches an utterance under analysis with a linguistically equivalent baseline utterance defined by subword models or word models which are built from subword models with predefined word lexicon. The recognized word or subword units are used to construct the whole word sequence with the help of language models. A continuous speech recognition system can recognize an entire sentence by first constructing a finite-state network, with or without a grammar-based language model, to represent the possible sentence model. Although the system 100 is based on a pattern recognition speech recognition approach, it is to be understood that the system may be implemented using other speech recognition approaches, such as the acoustic-phonetic or artificial intelligence approaches.

As illustrated, the speech processing system 100 includes: an analog to digital (A/D) converter 208 to convert the received audio signal into a digital audio signal, a speech detector 212 to determine when a received audio signal includes speech, a pre-filter unit 216 to effect front-end signal processing such as pre-emphasis, blocking and windowing (or frame separation), spectral analysis, feature extraction/enhancement, normalization, banding, and/or reduction of information rate and feature dimension, a frame analysis unit 220 to effect comparison and matching against baseline speech samples and recognition of the speech signal, an audio and/or video user interface 224 to interact with the user, a library 228 containing matching rules (such as pronunciation and inflection rules, grammar rules, words and corresponding phonetic parameters) and/or other acoustic characterizations (such as phonemes, diphones, triphones, tetraphones, or actual recorded speech samples) and optionally exceptions thereto, and a system clock 240 to provide timing information to the frame analyzer 220 and the other system components. It should be appreciated that the blocks illustrated in FIG. 1 are functional in nature and do not necessarily correspond to discrete hardware elements. In one embodiment, for example, the functionality 144 is implemented within a single digital processing device. Hardware implementations, however, are also possible.

With continuing reference to FIG. 2, the analog speech signal received at port 204 is first sampled and digitized within the A/D converter 208 to generate a digital waveform for delivery to the speech detector 212. If the waveform contains an utterance, it is forwarded to the pre-filter unit 216.

The pre-filter unit 216 performs any of a number of possible operations depending on the particular system configuration. In pre-emphasis, the unit 216 pre-emphasizes the waveform in a manner determined by the speech production model. The spectrum of the waveform is normally flattened by the unit 216. In blocking and windowing, the unit 216 extracts the short-time features of the waveform by blocking the speech waveform into short segments called frames. The duration of each frame normally ranges from about 10 to about 30 ms and may contain one or more utterance components. The speech belonging to each frame is assumed to be stationary. To reduce the edge effect of each frame, a smoothing window (e.g., a Hammering window) is applied to each frame. Generally, each successive frame overlaps the next to generate a smoother feature set over time. Each frame has a corresponding timestamp indicating when the utterance in the frame was received by the functionality. In temporal feature extraction, features of speech are extracted from each frame in the time domain. The temporal features include short-time average energy and amplitude, short-time zero-crossing rate, short-time autocorrelation, pitch periods, root mean square (rms), maximum of amplitude, voicing quality, difference between maximum and minimum values in the positive and negative halves of the signal, sound or utterance component type, and autocorrelation peaks. In spectral analysis, the waveforms in each frame are spectrally analyzed to extract spectral information of speech. Spectral analysis can be performed using any suitable algorithm such as a mel scale FFT filter-bank, perceptual linear predictive front-end, and auditory models. In extraction and enhancement of features, the obtained spectral information is processed by extracting useful features. The features in the frequency domain may include the difference between peak and valley, the energy in a particular frequency region, the spectral gradient and spectral variation contour, and the like. In reduction of information rate and feature dimension, the rate of generation of the feature vectors is reduced.

The frame analyzer 220 receives the frames from the pre-filter 216 and compares and matches the waveform (which includes a set of speech units) in each frame against baseline library entries.

Once the corresponding baseline speech units are identified, the frame analyzer 220 can perform one or different types of analysis. In a first type of analysis, the frame analyzer 220 attempts to match the speech units in each frame with baseline speech units in the library 228 and thereby recognizes the corresponding baseline speech waveform, or component speech units, for each frame. As will be appreciated, the frame analyzer 220 may use any comparison and/or matching algorithm, whether performing discrete or isolated, continuous, or spontaneous word recognition. Examples of such algorithms include Hidden Markov Models (HMM), frequency analysis, differential analysis, linear algebra techniques/shortcuts, spectral distortion, and time distortion methods.

Matching is typically done by mapping speech units in the utterance assuming first that the user is in a normal physical state and second that the user is in an altered physical state. In the first case, the match is performed assuming that the speech units were properly spoken. In the second case, the match is performed assuming that certain types of speech units were not properly spoken. The results of applying each of the two cases is compared with a controlling speech model to determine which set of possible speech units conforms with the speech model. For example, the speech unit resembling "l" would first be matched with "l" and then matched with "r", "sh" with "sh" and then with "s", and "ez" with "ez" and then with "es". Based on the comparison and degree of conformance of the two cases with the speech model, the frame analyzer 220 generates a probability that each case is correct and selects the case having the highest probability as being correct. The frame analyzer 220 can then apply selected linguistic measures, such as speech errors and nonfluency level, and aspects of speech quality.

In another configuration, the frame analyzer 220 performs frame-by-frame acoustic analysis for fundamental frequency (pitch or F0), formant or F-pattern, speech and/or articulation rate, vocal intensity (loudness), and response time assuming that the subscriber is correctly speaking the speech units. As will be appreciated, each frame has a corresponding selected timestamp. This permits the analyzer 120 to apply time-based measures, such as speech and/or acoustic rate.

Figure 3:
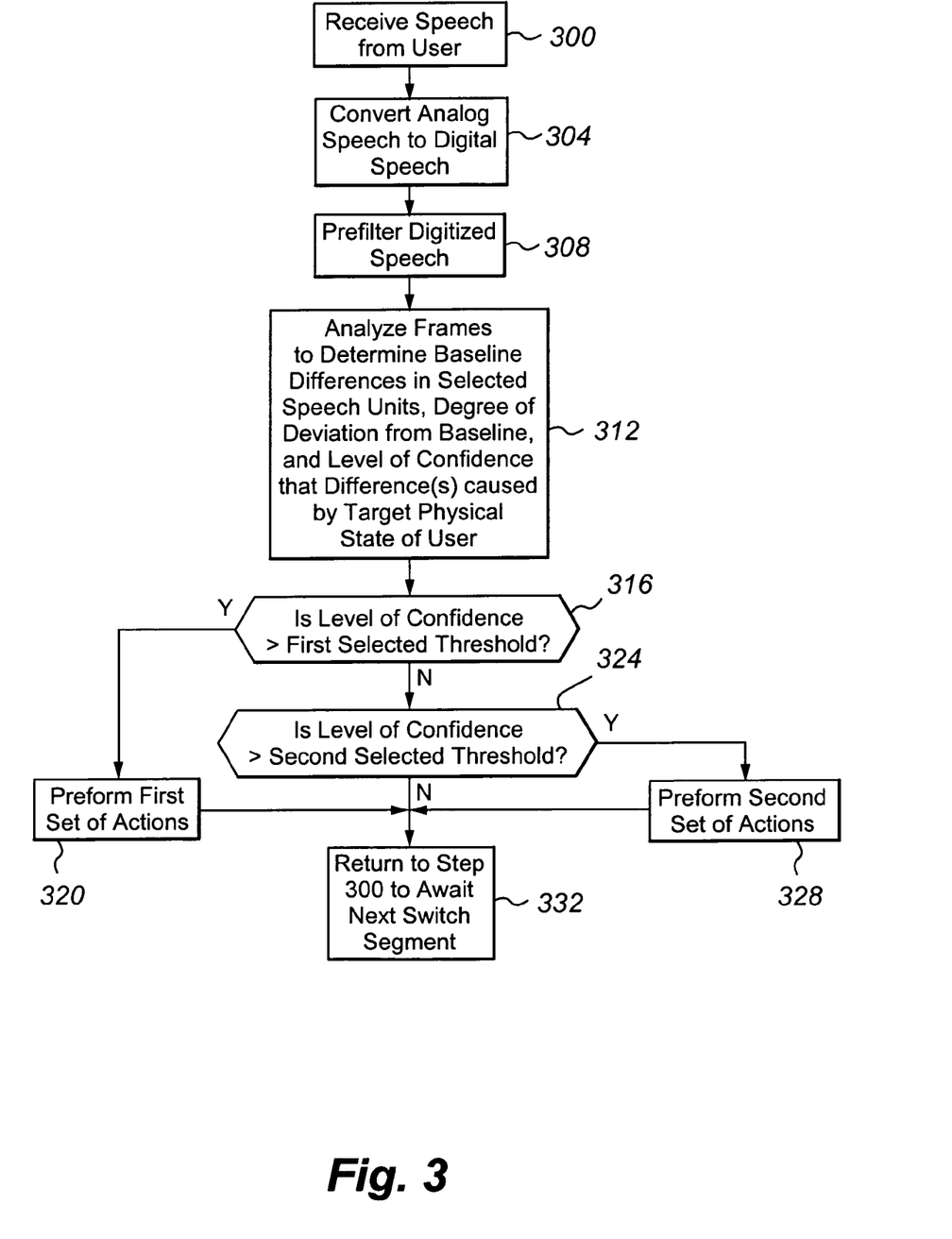
FIG. 3 is a flowchart depicting the operation of the user diagnostic functionality according to an embodiment of the present invention.

An operation of the functionality 144 will now be described with reference to FIG. 3. This figure assumes that the user has been authenticated successfully as the user potentially having the specified type of physical condition and for whom baseline recordings are available. In this manner, the speech processing system 100 will not conclude that a problem potentially exists simply because another user uses the communication device and therefore deviates from the baseline recording.

In step 300, the input port 204 receives an utterance from the user.

In step 304, the utterance is converted by the A/D converter 208 from analog to digital form.

In step 308, the prefilter 216 prefilters the digitized utterance and forms the utterance into frames.

In step 312, the frame analyzer 220 receives a (next) frame and corresponding timestamp from the pre-filter. The analyzer 220 may additionally receive an utterance component identifier indicating a type of utterance component (or speech unit) in the frame. The frame analyzer 220 determines a set of levels of confidence that the speaker has a specified type of physical condition (e.g., hypoglycemia, hyperglycemia, and/or normal) and, if the level of confidence is above a selected value, a likely degree of severity, or level, of the physical condition. In one configuration, the analyzer 220 outputs a first level of confidence that the user has hypoglycemia and a second level of confidence that the user has hyperglycemia.

In decision diamond 316, the analyzer 220 determines whether the set of level(s) of confidence that the user has a target condition is/are greater than a first set of selected threshold(s). The first set of selected threshold(s) indicate(s) a compelling likelihood that the user has a target medical condition.

If so, the functionality 144, in step 320, performs a first set of actions. In selecting the action to be taken, the analyzer 220 considers the likely degree of severity, or level, of the target physical condition. If the degree of severity or level is high, the functionality 144 notifies a nearby employee or primary caregiver to check on the condition of the subscriber and/or notifies emergency personnel that the subscriber may be suffering from extreme hypoglycemia or hyperglycemia. If the degree of severity or level is lower, the analyzer 220 suggests to the user a recommended course of action (e.g., checking blood sugar levels immediately, contacting a primary caregiver, etc.).

In decision diamond 324, the analyzer 220 determines if the set of level(s) of confidence, though less than the first set of selected threshold(s), is more than a second set of selected threshold(s). If the set of levels of confidence is/are more than the second set of selected threshold(s), the functionality 144, in step 328 performs a second set of actions. Because the second set of threshold(s) indicate(s) that there is a substantial, but not compelling, likelihood that the user may have a target physical condition, the action performed is generally one of visually and/or auditorally notifying the user of the determination (e.g., "Your blood sugar may be low", "Your blood sugar may be high", or simply, "Please check your blood sugar.").

If the set of levels of confidence is/are less than the second set of selected threshold(s) or after performing one of steps 320 and 328, the functionality 144 proceeds to step 332 and returns to step 300 to await the next speech segment.

A number of variations and modifications of the invention can be used. It would be possible to provide for some features of the invention without providing others.

For example in one alternative embodiment, the user diagnostic functionality 144 is included in an adjunct to the switch/server 108.

In another alternative embodiment, the user diagnostic functionality 144 is included in the communication device itself, such as in any of the communication devices 120, 124, and 128.

In yet another embodiment, dedicated hardware implementations including, but not limited to, Application Specific Integrated Circuits or ASICs, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be stated that the software implementations of the present invention are optionally stored on a tangible storage medium, such as a magnetic medium like a disk or tape, a magneto-optical or optical medium like a disk, or a solid state medium like a memory card or other package that houses one or more read-only (non-volatile) memories. A digital file attachment to e-mail or other self-contained information archive or set of archives is considered a distribution medium equivalent to a tangible storage medium. Accordingly, the invention is considered to include a tangible storage medium or distribution medium and prior art-recognized equivalents and successor media, in which the software implementations of the present invention are stored.

Although the present invention describes components and functions implemented in the embodiments with reference to particular standards and protocols, the invention is not limited to such standards and protocols. Other similar standards and protocols not mentioned herein are in existence and are considered to be included in the present invention. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present invention.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for determining a physical state of a user, comprising:
   receiving via communication device a voice utterance from a first speaker in a communication between the first speaker and a second speaker;
   analyzing the voice utterance to determine whether the first speaker likely has one of hypoglycemia or hyperglycemia, wherein if first speaker if speaking rapidly the first speaker is determined to be experiencing hypoglycemia and wherein if the first speaker is speaking lethargically, the first speaker is determined to be experiencing hyperglycemia;
   when the first speaker likely has one of hypoglycemia or hyperglycemia, at least one of:
   (i) sending to the user a notification associated with one of hypoglycemia or hyperglycemia, wherein the notification alerts the first speaker as to which of hypoglycemia or hyperglycemia the first speaker is suffering, and
   (ii) sending to a third party a notification associated with one of hypoglycemia or hyperglycemia, wherein the notification provides which of hypoglycemia or hyperglycemia the first speaker is suffering.

2. The method of claim 1, wherein analyzing the voice utterance comprises performing acoustic-phonetic analysis of the voice utterance to determine a likelihood that the first speaker has the target physical condition or a likely severity of the target physical condition.

3. The method of claim 1, wherein the acoustic-phonetic analysis analyzes, with reference to a baseline utterance of the first speaker, at least one of a formant of the utterance, a pitch of the utterance, a speech or articulation rate of the utterance, a vocal intensity of the utterance, a number of speech errors in the utterance, a response time, a nonfluency level associated with the utterance, and a speech quality of the utterance.

4. The method of claim 1, wherein the likelihood that the first speaker has the target physical condition and likely severity of the target physical condition are determined, wherein step (ii) is performed when the likelihood and likely severity are at least a first set of thresholds and wherein step (i) but not step (ii) is performed when at least one of the likelihood and likely severity is less than the first set of thresholds but more than a second set of thresholds.

5. The method of claim 1, wherein analyzing the voice utterance comprises:
   comparing speech units in the utterance with corresponding baseline speech units from the first speaker assuming that the first speaker does not have the target physical condition;
   comparing speech units in the utterance with corresponding baseline speech units from the first speaker assuming that the first speaker has the target physical condition; and
   based on the comparative results of substeps (b1) and (b2), determining a level of confidence that the first speaker has or does not have the target physical condition.

6. A non-transitory computer readable medium comprising thereon processor executable instructions to perform the steps of claim 1.

7. A communication device, comprising:
   a user diagnostic functionality operable to:
   (a) receive, as part of a voicemail, a voice utterance from a speaker;
   (b) analyze the voice utterance to determine whether the speaker likely has one of hypoglycemia or hyperglycemia, wherein if the speaker is speaking rapidly, the first speaker is determined to be experiencing hypoglycemia, and wherein if the first speaker is speaking lethargically, the first speaker is determined to be experiencing hyperglycemia; and
   (c) when the speaker likely has one of hypoglycemia or hyperglycemia, at least one of:
   (i) send to the user a notification associated with one of hypoglycemia or hyperglycemia, and
   (ii) send, to a third party, a notification associated with one of hypoglycemia or hyperglycemia.

8. The communication device of claim 7, wherein operation (b) comprises the sub-operation: (b1) performing acoustic-phonetic analysis of the voice utterance to determine a likelihood that the speaker has the target physical condition or a likely severity of the target physical condition.

9. The communication device of claim 7, wherein the acoustic-phonetic analysis analyzes, with reference to a baseline utterance of the speaker, at least one of a formant of the utterance, a pitch of the utterance, a speech or articulation rate of the utterance, a vocal intensity of the utterance, a number of speech errors in the utterance, a response time, a nonfluency level associated with the utterance, and a speech quality of the utterance.

10. The communication device of claim 7, wherein the likelihood that the speaker has the target physical condition and likely severity of the target physical condition are determined, wherein step (ii) is performed when the likelihood and likely severity are at least a first set of thresholds and wherein step (i) but not step (ii) is performed when at least one of the likelihood and likely severity is less than the first set of thresholds but more than a second set of thresholds.

11. The communication device of claim 7, wherein operation (b) comprises the sub-operations:
   (b1) comparing speech units in the utterance with corresponding baseline speech units from the speaker assuming that the speaker does not have the target physical condition;
   (b2) comparing speech units in the utterance with corresponding baseline speech units from the speaker assuming that the speaker has the target physical condition; and
   (b3) based on the comparative results of sub-operations (b1) and (b2), determining a level of confidence that the speaker has or does not have the target physical condition.

12. A method, comprising:
   receiving, by a communication device, a voice utterance from a speaker; sending the voice utterance to a communication node; and
   analyzing, by a communication node, the voice utterance to determine whether the speaker likely has one of hypoglycemia or hyperglycemia, wherein if the speaker is speaking rapidly it is determined that the speaker is experiencing hypoglycemia, and wherein if the speaker is speaking lethargically it is determined that the speaker is experiencing hyperglycemia.

13. The method of claim 12, wherein the voice utterance is received during a live conversation with another party and wherein, when the speaker likely has hypoglycemia and hyperglycemia, at least one of (i) sending to the user a notification associated with the hyperglycemia or hypoglycemia and (ii) sending to a third party a notification associated with the hyperglycemia or hypoglycemia.

14. The method of claim 13, wherein analyzing the voice utterance comprises performing acoustic-phonetic analysis of the voice utterance to determine a likelihood that the speaker has hyperglycemia or hypoglycemia or a likely severity of the hyperglycemia or hypoglycemia.

15. The method claim 14, wherein the acoustic-phonetic analysis analyzes, with reference to a baseline utterance of the speaker, at least one of a formant of the utterance, a pitch of the utterance, a speech or articulation rate of the utterance, a vocal intensity of the utterance, a number of speech errors in the utterance, a response time, a nonfluency level associated with the utterance, and a speech quality of the utterance.

16. The method of claim 13, wherein analyzing the voice utterance comprises:

comparing speech units in the utterance with corresponding baseline speech units from the speaker assuming that the speaker does not have hyperglycemia or hypoglycemia;

comparing speech units in the utterance with corresponding baseline speech units from the speaker assuming that the speaker has hyperglycemia or hypoglycemia; and based on the comparative results of the above comparing sub-steps, determining a level of confidence that the speaker has or does not have hyperglycemia or hypoglycemia.

17. The method of claim 13, wherein the likelihood that the speaker has hyperglycemia or hypoglycemia and likely severity of the hyperglycemia or hypoglycemia are determined, wherein step (ii) is performed when the likelihood and likely severity are at least a first set of thresholds and wherein step (i) but not step (ii) is performed when at least one of the likelihood and likely severity is less than the first set of thresholds but more than a second set of thresholds.

18. A non-transitory computer readable medium comprising thereon processor-executable instructions to perform the steps of claim 12.

* * * * *

UNITED STATES PATENT AND TRADEMARK OFFICE
CERTIFICATE OF CORRECTION

| | | |
|---|---|---|
| PATENT NO. | : 7,925,508 B1 | |
| APPLICATION NO. | : 11/508477 | |
| DATED | : April 12, 2011 | |
| INVENTOR(S) | : Michaelis | |

It is certified that error appears in the above-identified patent and that said Letters Patent is hereby corrected as shown below:

At column 11, line 22, "wherein if first speaker if" should be changed to --wherein if first speaker is--.

Signed and Sealed this
Thirteenth Day of September, 2011

David J. Kappos
*Director of the United States Patent and Trademark Office*